United States Patent
Unčovský et al.

(10) Patent No.: US 9,618,463 B2
(45) Date of Patent: Apr. 11, 2017

(54) METHOD OF ACQUIRING EBSP PATTERNS

(71) Applicant: FEI Company, Hillsboro, OR (US)

(72) Inventors: Marek Unčovský, Brno (CZ); Pavel Stejskal, Brno (CZ); Tomáš Vystavěl, Brno (CZ)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/834,069

(22) Filed: Aug. 24, 2015

(65) Prior Publication Data
US 2016/0054240 A1   Feb. 25, 2016

(30) Foreign Application Priority Data
Aug. 25, 2014   (EP) .................................... 14182139

(51) Int. Cl.
*H01J 37/26* (2006.01)
*G01N 23/203* (2006.01)
(Continued)

(52) U.S. Cl.
CPC .......... *G01N 23/203* (2013.01); *H01J 37/244* (2013.01); *H01J 37/252* (2013.01);
(Continued)

(58) Field of Classification Search
CPC .................. G01N 23/203; H01J 37/244; H01J 2237/24475; H01J 37/252;
(Continued)

(56) References Cited

U.S. PATENT DOCUMENTS 8,502,155 B2    8/2013  Ballabriga et al.
2006/0231752 A1*  10/2006  Houge ............... H01J 37/295
                                                        250/306
(Continued)

FOREIGN PATENT DOCUMENTS

EP          2151847      2/2010
WO       2013050788      4/2013

OTHER PUBLICATIONS

Deal et al., "Energy-filtered Electron Backscatter Diffraction", Ultramicroscopy, vol. 108, No. 2, Dec. 10, 2007, pp. 116-125.
(Continued)

*Primary Examiner* — Nicole Ippolito
(74) *Attorney, Agent, or Firm* — Scheinberg & Associates, P.C.; Michael O. Scheinberg

(57) ABSTRACT

The invention relates to a method of acquiring an Energy Backscattering Pattern image of a sample in a charged particle apparatus, the sample showing a flat surface, the charged particle apparatus equipped with an electron column for producing a finely focused electron beam, a position sensitive detector for detecting EBSP patterns, and a sample holder for holding and positioning the sample, the method comprising the steps of:

Figure 1:
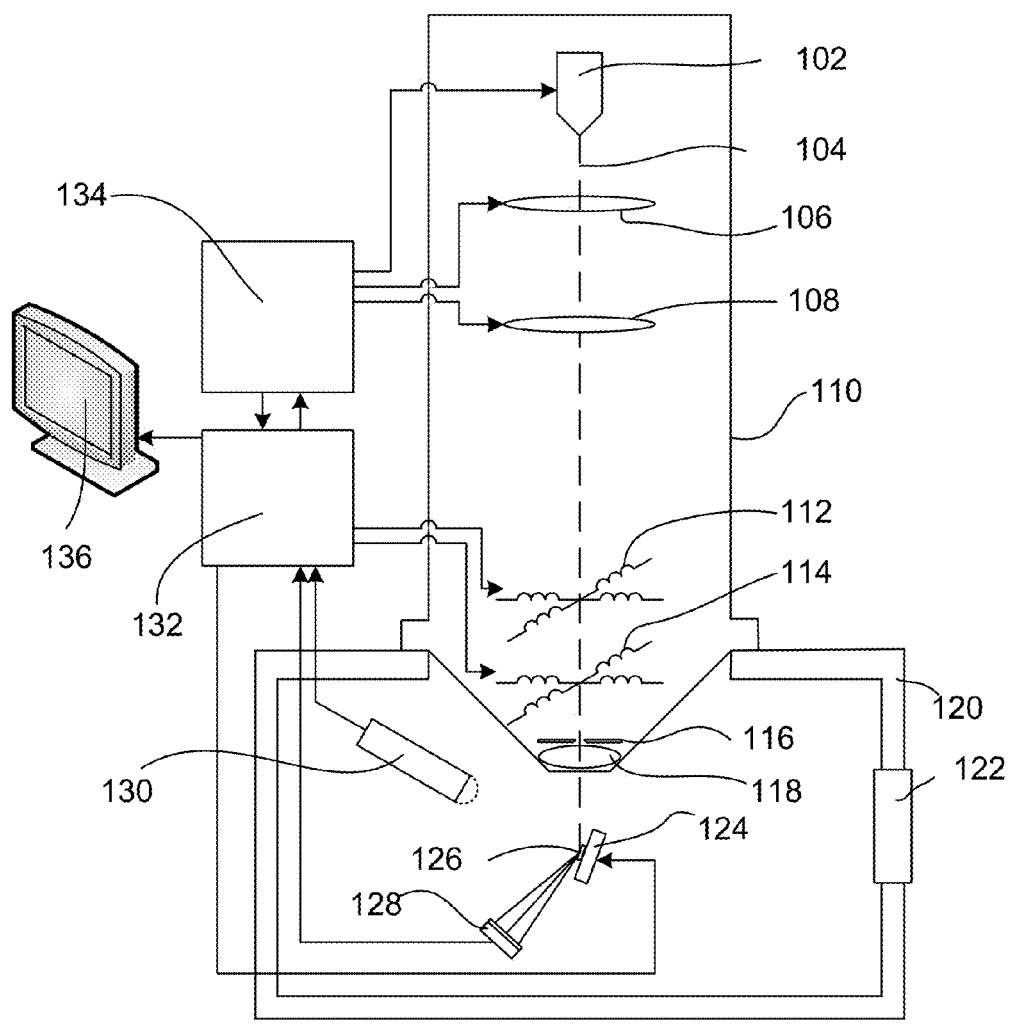

Positioning the sample with respect to the electron beam,
Directing the electron beam to an impact point on the sample, thereby causing backscattered electrons to irradiate the detector, and
Acquiring the signal from the detector while the beam is kept stationary, in which
The detector is equipped to selectively detect electrons with an energy above a predefined threshold, and
The signal of the electrons with an energy above said threshold is used to form an EBSP image.

20 Claims, 4 Drawing Sheets

(51) Int. Cl.
*H01J 37/244* (2006.01)
*H01J 37/252* (2006.01)

(52) U.S. Cl.
CPC .......... *H01J 2237/2442* (2013.01); *H01J 2237/2446* (2013.01); *H01J 2237/24475* (2013.01); *H01J 2237/24485* (2013.01); *H01J 2237/24495* (2013.01); *H01J 2237/24585* (2013.01); *H01J 2237/2555* (2013.01); *H01J 2237/31745* (2013.01)

(58) Field of Classification Search
CPC ....... H01J 2237/2442; H01J 2237/2446; H01J 2237/24485; H01J 2237/24495; H01J 2237/24585; H01J 2237/2555; H01J 2237/31745
USPC .............. 250/305, 306, 307, 309, 310, 311
See application file for complete search history.

(56) References Cited

U.S. PATENT DOCUMENTS

2008/0099674 A1* 5/2008 Bihr .................. G03F 1/72
250/307
2011/0186734 A1 8/2011 Hasuda et al.

OTHER PUBLICATIONS

S. Dabritz et al., "Kossel and Pseudo Kossel CCD Pattern in Comparison with Electron Backscattering Diffraction Diagrams", Applied Surface Science. vol. 179, No. 1-4, Jul. 1, 2001, 7 pages.
European Patent Office Communication pursuant to Article 94(3) EPC dated Feb. 6, 2017 related to European application No. 15182001.6.
Farrer, J.K., et al., "EBSD Pattern Collection and Orientation Mapping at Normal Incidence to the Electron Beam," Microsc Microanal (2003), pp. 80-81, vol. 9, Suppl. 2.
Keller, R.R., et al., "Transmission EBSD from 10 nm domains in a scanning electron microscope," Journal of Microscopy (2011), 7 pgs.
Third-party observations submitted to European Patent Office on Sep. 28, 2016 in relation to European patent application No. 15182001.6.
Venables, J.A., et al., "Electron back-scattering patterns—A new technique for obtaining crystallographic information in the scanning electron microscope," Philosophical Magazine, (1973), pp. 1193-1200, vol. 27, Issue 5.

* cited by examiner

METHOD OF ACQUIRING EBSP PATTERNS

The invention relates to a method of acquiring an Electron Backscattered Pattern (EBSP) image of a sample in a charged particle apparatus, the sample showing a flat surface, the charged particle apparatus equipped with an electron column for producing a finely focused electron beam, a position sensitive detector for detecting Electron Backscattering Patterns, and a sample holder for holding and positioning the sample, the method comprising the steps of positioning the sample with respect to the electron beam, directing the electron beam to an impact point on the sample, thereby causing backscattered electrons to irradiate the detector, and acquiring the signal from the detector while the beam is kept stationary.

This method is well-known to the skilled artisan and is described in, for example, "Scanning Electron Microscopy", L. Reimer, Springer Verlag (1985), ISBN 3-540-13530-8, more specifically chapter 8.3: "Electron Diffraction Effects Associated with Scattered Electrons", most specifically chapter 8.3.2: "Electron Backscattered Patterns (EBSP)".

When an electron beam impinges on ("hits") a sample, backscattered electrons (BSEs) emerge from the sample.

It is noted that BSEs are generally defined as electrons emerging from the sample with an energy of more than 50 eV, contrary to secondary electrons (SEs), which are generated likewise but have an energy of less than 50 eV.

It is further noted that an Electron Backscattered Pattern image is also referred to as an Electron Backscattered Diffraction image.

When using a (multi)crystalline sample, for example a metal, the BSEs can be detected by detecting their impact on a position sensitive detector, such as a fluorescent screen that is coupled to a camera, or a pixilated detector such as a CCD or CMOS chip. The BSEs do not emerge from the sample in all directions with the same intensity/probability. Among other effects, in certain directions the intensity is larger due to preferential reflection on the crystal lattice, and thereby so-called Kikuchi lines are formed on the detector. The direction in which the Kikuchi-lines are formed is a function of the direction of the impinging beam and the crystallographic axes and the type of unit cell (cubic, body-centered cubic, face-centered cubic, hexagonal, etc.) of the sample. An image of the Kikuchi lines is typically formed using a polished (thus: flat) sample while the beam is kept stationary on the sample. From the Kikuchi lines formed on the detector the crystallographic orientation of the irradiated point and the type of unit cell can be derived, as well as the form of the unit cell. By repeating the imaging for many points, a map can be made of the crystallographic orientations and crystal types of (micro)crystals in the sample.

The intensity variations caused by the Kikuchi lines are small variations and are most prominent when the beam of electrons impinges on the (crystalline) sample under a slanted angle, that is: the angle between the normal of the (polished) flat surface of the sample and the impinging beam is preferably between 60 to 80 degrees. This is also referred to as a 60 to 80 degrees tilt of the sample with respect to the beam.

The reason for this slanted, almost glancing, angle is that it is well known that, when recording the Kikuchi lines, only for this incident angle, and for reflections under an angle of at least 90 degrees with respect to the incoming electron beam, an acceptable contrast of the Kikuchi lines occurs.

It is noted that it is equally well known that the contrast improves when increasing the energy of the impinging electrons.

An example of an instrument for performing the known method is the CamScan X500, commercially sold by Obducat CamScan Limited, CamScan House, Pembroke Avenue, Waterbeach, Cambridge, CB25 9PY UK, and described in http://www.lot-oriel.com/files/downloads/camscan/eu/Crystal_Probe_X500.pdf This instrument is designed to inspect molten or almost molten samples, which have to be kept horizontal to avoid movement ("dripping") of the liquid or semi-liquid due to gravitational forces. As the sample can thus not be tilted the instrument is equipped with an electron column slanted under an angle of 70 degrees with respect to the vertical direction, thus enabling inspection of the sample under earlier mentioned angled electron beam while the surface of the sample is horizontally oriented.

As known to the person skilled in the art, a non-vertical electron column implies a specially designed electron column, which is more prone to vibrations etc. Each vertical acceleration results in bending of the column and thus displacement of the spot, and possibly even displacement of optical parts of the column, resulting in mis-alignments and thus deteriorated optical performance.

"Scanning Microscopy for nanotechnology—techniques and applications", W. Zhou et al. (Eds), (2007), ISBN: 978-0-387-33325-0, more specifically Chapter 2: "Electron Backscatter Diffraction (EBSD) Technique and Materials Characterization Examples", T. Maitland et al., pages 41-75, describes the history and the recent use of EBSP.

Figure 2:
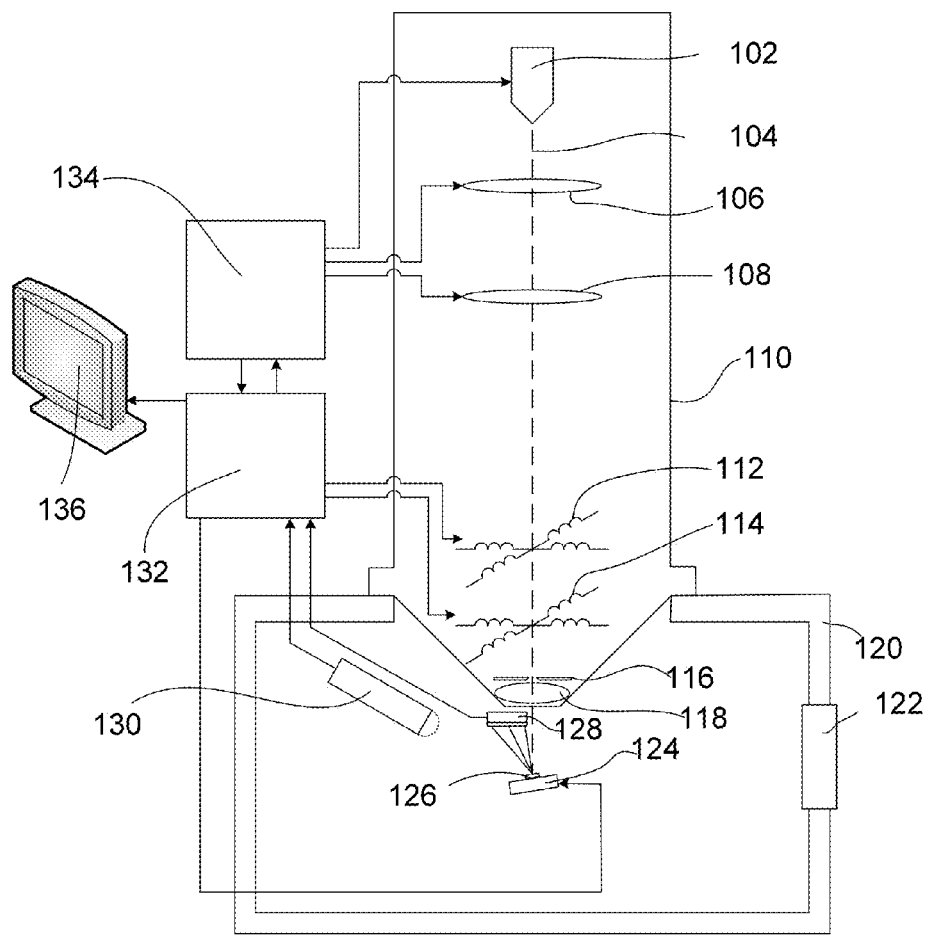

In Paragraph 1.2 "How it works?" of said chapter it is described that EBSD operates by arranging a flat, highly polished (or as-deposited thin film) sample at a shallow angle, usually 20 degrees, to the incident electron beam (see FIG. 2.7 of said publication). As the shallow angle is realized by tilting the sample, this is normally referred to as a tilt of typically 70°.

As known to the skilled person, finding a place of interest on a highly tilted sample is difficult as this is normally done by imaging the sample and then, using so-called spot mode, keeping the beam stationary at a selected position. However, imaging on a highly tilted sample is often associated with a loss of focus at certain positions, while even relative minor charging of (parts of the) sample results in severe displacement of the beam.

There is a need for high quality EBSP imaging without using high tilt angles, that is, tilt angles of more than 45 degrees.

The invention intends to provide a solution to that.

To that end the method according to the invention is characterized in that the position sensitive detector is equipped to selectively detect electrons with an energy above a predefined threshold, and only the signal of the electrons with an energy above said threshold is used to form an EBSP image.

Inventors found surprisingly that this energy filtered signal acquired in low tilt configuration enables EBSP imaging with significantly improved resolution and better contrast of formed Kikuchi lines. This is contrary to the already long existing prejudice that only by a beam impinging on the sample at a large angle from the normal to the sample (thus: almost glancing) results in a good image.

In principle an energy filtered signal can be achieved by filtering the BSEs. However, filtering BSEs also influences the angular angles under which the BSEs emerge from the sample and is therefore not or hardly used for position sensitive BSE detectors, as this introduces large distortions.

It is mentioned that the phrase "position sensitive detector" or "position dependent detector" is used here to describe a detector that as an output signal has a multi-pixel signal, each pixel representing an area on the detector. Such pixelated detectors are for example camera's observing a fluorescent screen, or otherwise coupled to said screen (e.g. using optical fibers), or for example a CMOS or CCD chip for direct detection of electrons.

Inventors recognized that positional sensitive detectors (position dependent detector) that also give information of the energy of the detected electrons can give the required signal. Such detectors are known as, for example, Medipix® or Timepix® detectors (developed by a consortium headed by CERN, see http://medipix.web.cern.ch/medipix/) and described in e.g. U.S. Pat. No. 8,502,155.

Preferably the detector is a pixelated detector.

In an embodiment during acquisition of the image the angle between the normal to the flat surface of the sample and the electron beam is less than 45 degrees.

A tilt angle of less than 45 degrees (that is: the angle between the normal to the samples surface and the incident beam is less than 45 degrees) enables tilt even when the sample is close to the column producing the electron beam (working at a small working distance), without bumping to the objective lens. As known to the skilled person this small working distance results in a high resolution of the image formed (due to a small spot size of the electron beam), and—given a diameter of the detector/sensor—in a large acceptance angle of the detector/sensor, and thus a large visible part of the Kikuchi patterns.

In another embodiment the detector is equipped to detect electrons in different energy bands.

By using a detector capable to detect electron's energy, as is possible in e.g. the Timepix® detector, it is possible to change the beam energy without reprogramming the energy threshold of the detector. This may be attractive to allow more electrons (for a better signal to noise ratio) or less electrons (for better energy selection).

In still another embodiment the detector is a detector with a sensor chip showing pixels for detecting backscattered electrons bonded to a chip comprising for each pixel an amplifier, a programmable comparator for energy discrimination, and a counter. Preferably the bonding is flip-chip bump bonding, This embodiment describes for example a Medipix2 or a Timepix® detector.

In yet another embodiment the beam has, during acquisition of the EBSP image, an energy of 5 keV or less.

In this embodiment a beam of electrons with a low energy is used. As the relative intensity, or contrast, of the EBSP image is known to decrease with decreasing beam energy, this is with prior art techniques not or hardly possible.

Using a prior art detector/set-up the problem is aggravated by the fact that prior art detectors typically use a fluorescent screen. Such a fluorescent screen gives a very noisy signal for low energy BSEs as the variation in the number of photons generated per BSE (per event) is then large. Inventors found that by using a detector with a programmable threshold good EBSP images could be obtained.

It is noted that it is known to use a detector with post-acceleration, but this distorts the Kikuchi patterns and is thus a difficult method, with drawbacks.

The advantages of low-energy EBSP are: lower penetration of the beam and thus more signal of the surface layer. This makes low-energy EBSP especially suited for analyzing thin films. Another advantage of low-energy EBSP is that there is less beam damage when inspecting fragile samples.

In yet another embodiment the method further comprises imaging the sample by scanning the beam over the sample, and detecting a signal from the group of SEs, BSEs, X-rays, or photons in the visible light.

By making a scanned image of the sample, the location of places of interest can be determined, and also the size of (micro)crystallites and grain boundaries can be determined.

In an aspect of the invention a charged particle apparatus equipped with an electron beam column and a pixelated detector for detecting an EBSP pattern, the apparatus characterized in that detector is equipped to selectively detect electrons with an energy above a predefined threshold, and that the apparatus is equipped with a programmable controller for controlling beam position and detector, said controller equipped to process the signal from the detector to form an EBSP image.

This aspect of the invention describes an apparatus to perform the method according to the invention.

In a further embodiment of the charged particle apparatus the programmable controller is equipped to automatically process the EBSP image to determine crystallographic orientation and form an image showing the crystallographic orientation of crystals of the sample.

In this embodiment the apparatus is not only equipped to form an EBSP pattern, but to form EBSP patterns on a multitude of positions and for each of these positions determine the crystallographic orientation (and type of unit cell) from the obtained EBSP pattern of the corresponding position.

It is noted that to further improve the analysis of the sample, X-ray detection can be used to determine the composition of the different crystallites and that the position of the grain boundaries between crystallites can be determined by, for example, making a scanned image of the sample. A change in intensity on such a scanned image indicated a boundary between crystallites.

In another embodiment the predefined threshold is a programmable predefined threshold.

By combination of images with different energy content (i.e. parallel acquisition of different energy bands) one can optimize speed of acquisition with respect to the contrast of Kikuchi patterns and thus improve throughput of the method, without restarting of acquisition and setting new threshold(s).

In yet another embodiment the charged particle apparatus further comprises an ion beam column for machining the sample before detecting the EBSP pattern.

Charged particle apparatuses comprising an ion beam column for producing a finely focused ion beam and an electron beam column for producing a finely focused electron beam are known to the skilled artisan, and commercially available from, for example, FEI Company, Hillsboro, Oreg., USA under the name DualBeam®. This embodiment enabled machining the sample in-situ by removing a surface layer for regions of interest, or to remove, for example, an oxidized surface. As the sample is imaged while the sample is in an evacuated environment, subsequent oxidation in said environment plays only a minor role.

In a further embodiment the charged particle apparatus further comprises a Gas Injection System for enhanced machining or etching of the sample.

As known to the skilled person the injection of fluids by a gas injection system can enhance the milling of the ion beam.

The invention is now elucidated using figures, in which identical reference numerals indicate corresponding features.

Figure 3A:
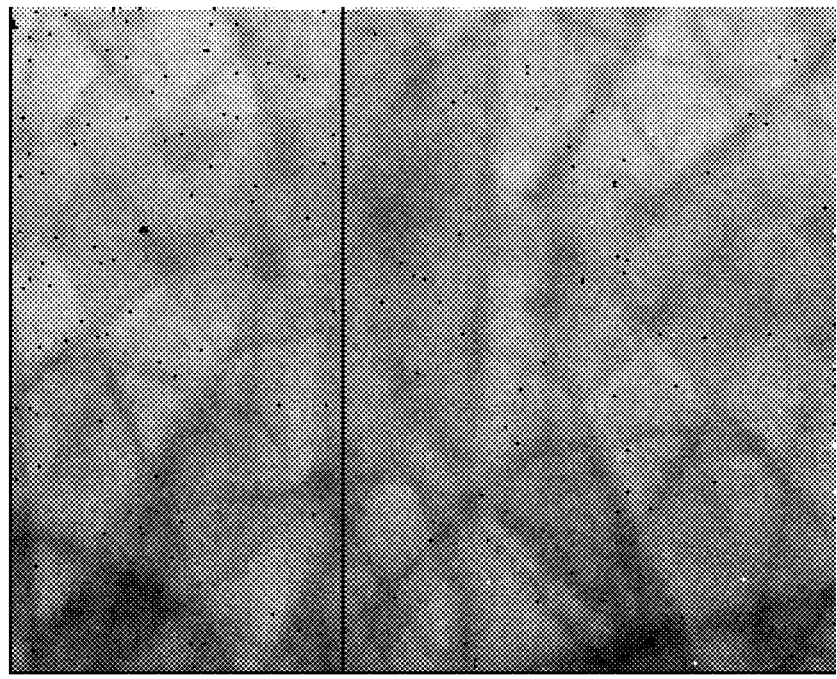
Figure 3B:
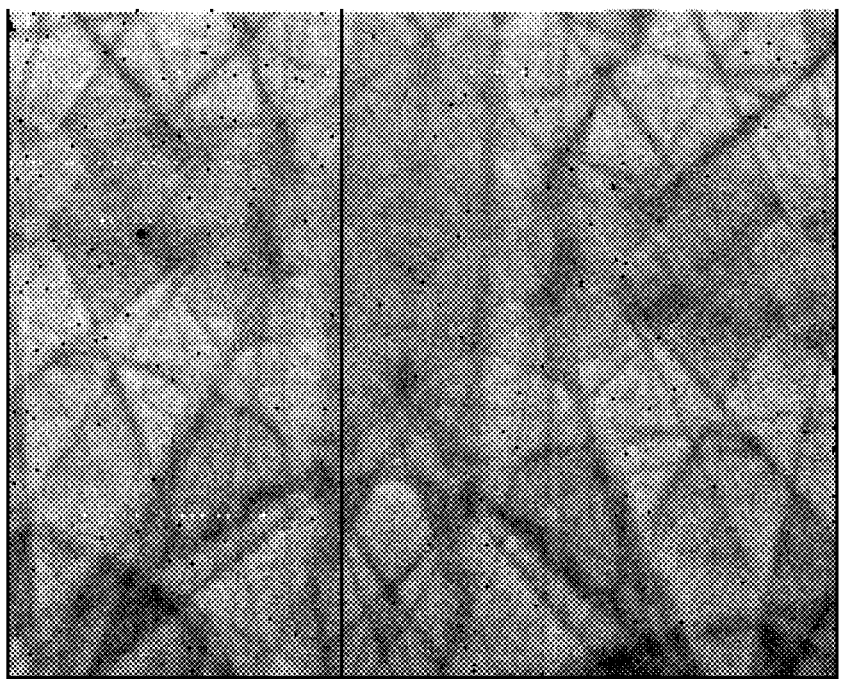
Figure 4:
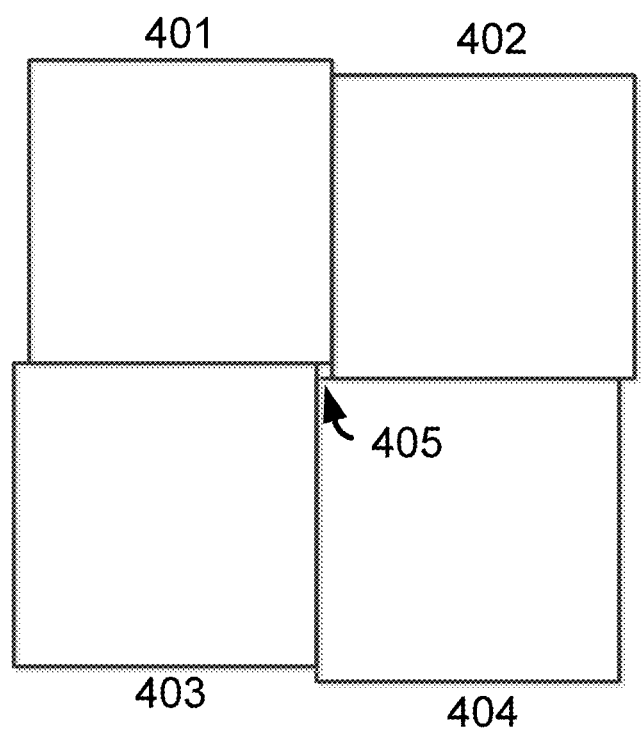

To that end:

FIG. 1 schematically shows a prior art EBSP set-up;

FIG. 2 schematically shows an EBSP set-up according to the invention;

FIG. 3a schematically shows an image acquired without energy filtering;

FIG. 3b schematically shows an image acquired with energy filtering;

FIG. 4 schematically shows an advantageous arrangement using four square detectors.

FIG. 1 schematically shows a prior art EBSP set-up.

FIG. 1 shows an electron beam column 110 placed on a sample chamber 120. The electron beam column comprising an electron source 102 for producing a beam of energetic electrons with a selectable energy of, for example, between 500 eV and 30 keV, along particle-optical axis 104. The beam of electrons is manipulated by lenses (106, 108, 118) and deflectors (112, 114) and beam limiting apertures (116) so as to form a finely focused spot on sample 126.

The sample chamber comprises an airlock 122 for introducing the sample therein and placing is on sample manipulator 124. The sample manipulator can manipulate (rotate, translate) the sample so that an area of interest is irradiated by the finely focused electron beam under a selectable tilt angle. The sample chamber further comprises one or more detector, such as an Everhart-Thornley detector (130) or an EBSP detector (128). Further both the electron beam column and the sample chamber are connected with high vacuum pump to evacuate the enclosed volumes.

The voltages and/or currents needed for the working of the (magnetic or electrostatic) lenses and of the electron source are generated/controlled by the column controller 134, while the signal controller/processor 132 generates deflection signals for the deflectors and samples the signals of the detectors. The signal controller/processor is also connected to a display unit 136 for displaying information, such an image of the sample, or for example the Kikuchi pattern acquired. The signal controller/processor (or another controller in communication with it) also controls the position and tilt of the sample by moving the sample manipulator.

EBSP detector 128 typically comprises a fluorescent screen (phosphor screen) and a CMOS or CCD camera chip. The fluorescent layer can be in direct contact with the camera chip, but in another embodiment of the detector a fiber-optical plate is placed between the two. In yet another embodiment the fluorescent screen is imaged on the camera chip by optical elements.

For obtaining an EBSP image a polished sample 126 is introduced in the sample chamber 120 of the particle-optical apparatus. The sample is then positioned so that a "normal" SEM image of the sample is made to identify an area of interest. Typically this implies that the sample is facing the column 110, and that the signal of the Everhart-Thornley detector is used, or another detector (for example another type of secondary electron detector or a backscattered electron detector). After identifying one or more areas of interest the sample is then tilted, typically to an angle of about 70 degrees, so that the beam impinges under a shallow angle of approximately 20 degrees on the sample. The beam is positioned stationary on one of the areas of interest and the signal of the EBSP detector is used to acquire an EBSP image. For viewing other parts of the Kikuchi patterns either the orientation of the sample is changed or the position of the detector is changed. After such a change a new EBSP image is acquired.

The image can either be shown on monitor 136, or using software running on the image controller 132 (or a computer connected to it) the crystallographic orientation of the area of interest is determined and displayed.

It is noted that finding the orientation of a crystallite is typically done by matching known EBSP patterns (or simulated versions thereof) with the observed EBSP patterns. Typically this is done by comparison of Hough transformed Kikuchi patterns (by peak detection), not by comparison of Kikuchi patterns themselves.

FIG. 2 schematically shows an EBSP set-up according to the invention.

FIG. 2 can be thought to be derived from FIG. 1. However, the EBSP detector 128 is exchanged by EBSP detector 138 that resides at another position. Also the orientation of the sample 126 during the acquisition of the EBSP pattern differs. This is enabled by the use of energy selection of the backscattered electrons. Inventors therefore coined the phrase Energy Selected EBSP or ES-EBSP for this technique. This enables normal SEM imaging and EBSP with identical or almost identical orientation of the sample. It also enables the detector 128 to be used as a standard BSE detector.

It is noted that the detector 138 is of another type than the detector 128 shown in FIG. 1. The EBSP detector 138 shown in FIG. 2 is an energy discriminating detector, and is preferably not equipped with a scintillator layer, but comprises a sensor in which the impinging BSEs cause the formation of electron/hole pairs. The number of electron/hole pairs per event (incoming electron) is a function of the energy of the impinging electron. The detector is equipped to detect this number of electron/hole pairs, and thus an estimation can be made of the energy of the incoming electron.

It is further noted that the sample can be horizontal, that is: the surface being perpendicular to the optical axis.

FIGS. 3A and 3B show test results of the method according to the invention

The method was tested using an existing Medipix2 detector with a possibility of one energy threshold only. The sensor was mounted on a Peltier cooler to improve the signal-to-noise ratio and its temperature was measured/stabilized using a Pt100 thermoresistor.

Both images where taken using a beam energy of 30 keV. FIG. 3A shows the image using all BSEs with an energy of at least 3 keV while FIG. 3B shows the image formed by all BSEs with an energy of at least 25 keV.

Comparing the two images it is easily seen that FIG. 3B shows much better defined Kikuchi lines.

It is noted that a test with an added plastic shield (fully stopping the electrons but not X-rays) confirmed that the pattern was an electron diffraction pattern, and not a so-named Kossel pattern.

It is noted that in FIG. 2 and in the set-up used to obtain the results of FIGS. 3A and 3B, only one detector, slightly off-axis, was used to acquire the signal. The person skilled in the art will readily recognize that a larger detector, or several detectors stitched together, enable the acquisition of a larger solid angle.

In FIG. 4 an advantageous arrangement using four square detectors is shown.

By arranging four square (or rectangular) detectors such, that a small hole is left through which the electron beam can pass, a composite detector is formed with a large acceptance angle. Detectors 401, 402, 403 and 404 are connected with the signal controller/processor. A small area 405 in the center is kept open for passing the beam of electrons.

It is noted that, although in this description the invention is explained referring to Medipix® and Timepix® detectors, this must not be seen as a limitation to the invention to only these detectors. Any electron detector that is both sufficiently position sensitive and sufficiently energy discriminating can be used.

The invention claimed is:

1. Method of acquiring an Electron Backscattering Pattern (EBSP) image and/or a Kossel image of a sample in a charged particle apparatus, the sample showing a flat surface, the charged particle apparatus equipped with an electron column for producing a finely focused electron beam, a position sensitive detector for detecting EBSP patterns and/or Kossel image, and a sample holder for holding and positioning the sample, the method comprising the steps of:
    positioning the sample with respect to the electron beam,
    directing the electron beam to an impact point on the sample, thereby causing backscattered electrons and/or X-rays to irradiate the detector, and
    acquiring the signal from the detector while the beam is kept stationary,
    the detector is equipped to selectively detect electrons and/or X-rays with an energy above a predefined threshold, and
    the signal of the electrons and/or X-rays with an energy above said threshold is used to form an EBSP or Kossel image,
    in which during acquisition of the image the angle between the normal to the flat surface of the sample and the electron beam is less than 45 degrees.

2. The method of claim 1 in which the detector is a pixelated detector.

3. The method of claim 2 in which the detector is equipped to detect electrons and/or X-rays within different energy bands.

4. The method of claim 2 in which during acquisition the electron beam has an energy of 5 keV or less.

5. The method of claim 2 in which the method further comprises imaging the sample while scanning the electron beam over the sample, and detecting a signal from the group of SEs, BSEs, X-rays, or photons in the visible light.

6. The method of claim 2 in which the predetermined threshold is a programmable predetermined threshold.

7. The method of claim 1 in which the detector is equipped to detect electrons and/or X-rays within different energy bands.

8. The method of claim 7 in which the detector is a detector with a sensor chip showing pixels on which the backscattered electrons and/or X-rays impinge is bonded to a chip comprising for each pixel an amplifier, a comparator and a counter.

9. The method of claim 8 in which the bonding is flip-chip bump bonding.

10. The method of claim 7 in which during acquisition the electron beam has an energy of 5 keV or less.

11. The method of claim 1 in which during acquisition the electron beam has an energy of 5 keV or less.

12. The method of claim 1 in which the method further comprises imaging the sample while scanning the electron beam over the sample, and detecting a signal from the group of SEs, BSEs, X-rays, or photons in the visible light.

13. The method of claim 1 in which the predetermined threshold is a programmable predetermined threshold.

14. A charged particle apparatus equipped with an electron beam column and a pixelated detector for detecting an EBSP pattern and/or a Kossel pattern, the apparatus characterized in that the detector is equipped to selectively detect electrons and/or X-rays with an energy above a predefined threshold, and that the apparatus is equipped with a programmable controller for controlling beam position and the detector, said controller further equipped to process the signal from the detector to form an EBSP image and/or a Kossel image, the apparatus including a sample holder for holding and positioning a sample such that, during acquisition of the image the angle between the normal to the flat surface of the sample and the electron beam is less than 45 degrees.

15. The charged particle apparatus of claim 14 in which the programmable controller is equipped to automatically process the EBSP or Kossel image to determine crystallographic orientation and form an image showing the crystallographic orientation of crystals of the sample.

16. The charged particle apparatus of claim 15 in which the predefined threshold is a programmable predefined threshold.

17. The charged particle apparatus of claim 15 in which the apparatus further comprises an ion beam column for machining the sample before detecting the EBSP pattern and/or the Kossel pattern.

18. The charged particle apparatus of claim 14 in which the predefined threshold is a programmable predefined threshold.

19. The charged particle apparatus of claim 14 in which the apparatus further comprises an ion beam column for machining the sample before detecting the EBSP pattern and/or the Kossel pattern.

20. The charged particle apparatus of claim 19 in which the apparatus further comprises a Gas Injection System for enhanced machining or etching of the sample.

* * * * *